(12) United States Patent
Jacobson et al.

(10) Patent No.: US 7,795,040 B2
(45) Date of Patent: Sep. 14, 2010

(54) METHODS, PARTICLES, AND KITS FOR DETERMINING ACTIVITY OF A KINASE

(75) Inventors: James W. Jacobson, Leander, TX (US); Ananda G. Lugade, Austin, TX (US); Michaela R. Hoffmeyer, Cedar Park, TX (US)

(73) Assignee: Luminex Corporation, Austin, TX (US)

( * ) Notice: Subject to any disclaimer, the term of this patent is extended or adjusted under 35 U.S.C. 154(b) by 391 days.

(21) Appl. No.: 11/736,254

(22) Filed: Apr. 17, 2007

(65) Prior Publication Data

US 2008/0026403 A1 Jan. 31, 2008

Related U.S. Application Data

(60) Provisional application No. 60/744,949, filed on Apr. 17, 2006.

(51) Int. Cl.
*G01N 33/543* (2006.01)
(52) U.S. Cl. ..................................... 436/518
(58) Field of Classification Search ................ None
See application file for complete search history.

(56) References Cited

U.S. PATENT DOCUMENTS

| | | | |
|---|---|---|---|
| 5,736,330 | A | 4/1998 | Fulton |
| 5,981,180 | A | 11/1999 | Chandler et al. |
| 6,046,807 | A | 4/2000 | Chandler |
| 6,057,107 | A | 5/2000 | Fulton |
| 6,139,800 | A | 10/2000 | Chandler |
| 6,268,222 | B1 | 7/2001 | Chandler et al. |
| 6,366,354 | B1 | 4/2002 | Chandler |
| 6,411,904 | B1 | 6/2002 | Chandler |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 2006/0105395 | A1 | 5/2006 | Pempsell |

FOREIGN PATENT DOCUMENTS

EP      1394270      3/2004

OTHER PUBLICATIONS

Parker et al. "Development of hight throughput screening assays using fluorescence polarization: nuclear receptor-ligand-binding and kinase/phosphatase assays", J Biomolecular Screening, 2000, 5(2):77-88.*
Rininsland et al. "Metal ion-mediated polymer superquenching for highly sensitive detection of kinase and phosphatase activities", PNAS, 2004, 101(43):15295-15300.*
Chen et al. "Design and synthesis of a fluorescent reporter of protein kinase activity", J. Am. Chem. Soc. 2002, 124:3840-3841.*
Minta et al. "Fluorescent indicators for cytosolic calcium based on rhodamine and fluorescein chrompphores", JBC, 1989, 264(14):8171-8178.*
Knight et al., "Phosphospecific proteolysis for mapping sites of protein phosphorylation," Nature Biotechnology, vol. 21, No. 9, Sep. 2003, pp. 1047-1054.
Akita et al, "On-Bead Fluorescence Assay for Serine/Threonine Kinases," Organic Letters, vol. 7, No. 25, 2005, pp. 5565-5568.
Shults et al., "Versatile Fluorescence Probes of Protein Kinase Activity," J. Am. Chem. Soc., vol. 125, No. 47, 2003, pp. 14248-14249.
Martin et al., "Quantitative analysis of protein phosphorylation status and protein kinase activity on microarrays using a novel fluorescent phosphorylation sensor dye," presented at Association of BioMolecular Resource Facilities, Feb. 2003, pp. 1-8.
Illum et al., "Attachment of Monoclonal Antibodies to Microspheres," Methods in Enzymology, vol. 112, 1985, pp. 67-84.
International Search Report, PCT/US2007/066781, mailed Oct. 29, 2007.

* cited by examiner

*Primary Examiner*—Karen Cochrane Carlson
*Assistant Examiner*—Bin Shen
(74) *Attorney, Agent, or Firm*—Charles D. Huston; Mollie E. Lettang; Daffer McDaniel, LLP (57) ABSTRACT

Methods, particles and kits for determining kinase activity within a sample are provided. An embodiment of a method includes exposing a fluorescent particle to an assay, wherein the fluorescent particle includes a support substrate having one or more fluorescent materials and a peptide substrate coupled to the support substrate via a functional group of the support substrate. The method further includes phosphorylating the peptide substrate during exposure of the fluorescent particle to the assay and processing the fluorescent particle such that the peptide substrate is dephosphorylated and a polarized double bond is generated at a dephosphorylated site. In addition, the method includes coupling a fluorescent reporter having a nucleophilic terminal group to the fluorescent particle via the polarized double bond.

18 Claims, 2 Drawing Sheets

METHODS, PARTICLES, AND KITS FOR DETERMINING ACTIVITY OF A KINASE

PRIORITY CLAIM

The present application claims priority to U.S. Provisional Application No. 60/744,949 filed Apr. 17, 2006.

BACKGROUND OF THE INVENTION

1. Field of the Invention

The present invention generally relates to methods and compositions (e.g., particles and kits) for determining activity of a kinase or kinases and, more specifically, to methods and compositions for determining activity/activities of one or more kinases coupled to particles in a multiplexing process using fluorescence detection.

2. Description of the Related Art

The following description and examples are not admitted to be prior art by virtue of their inclusion in this section.

Protein kinases play an important role in regulating cellular signal transduction within living organisms and readily occur in nature. For example, there are more than 500 protein kinases and over 500,000 human phosphorylation sites in the human genome. A protein kinase can be generally defined as an enzyme catalyzing the transfer of phosphate from adenosine triphosphate (ATP) to an amino acid residue. Abnormal expressions of protein phosphorylation events may be associated with several diseases and malignancies in living organisms, particularly humans. As such, monitoring protein kinase activity may be advantageous for detecting diseases and malignancies and/or identifying therapeutic agents for diseases and malignancies (i.e., therapeutic agents for promoting or inhibiting protein kinase activity within a living organism).

As apparent to one skilled in the art of microarray technology, it is generally advantageous to determine the presence and/or concentration of analytes within chemical and biological assays quickly. In addition or alternatively, it may be advantageous to evaluate multiple analytes simultaneously. The simultaneous evaluation of multiple analytes within a single sample is referred to herein as a multiplexing scheme. Conventional techniques for determining kinase activity are not typically suitable for high throughput screening and/or a multiplexing assay. In particular, many conventional techniques for determining kinase activity utilize radioactive isotopes and rely on liquid chromatography and/or mass spectrometry for analysis and, therefore, are not suitable for rapid examination. In addition, such methods do not continuously monitor kinase activity and, consequently, may not render an accurate determination of kinase activity. Other techniques for determining kinase activity involve expensive and specialized biological reagents such as phosphopeptide-specific antibodies. In general, antibody-based microarrays produce a large number of false positives and negatives due to the unpredictable cross-reactivity of antibodies. Consequently, antibody-based kinase activity techniques are generally not amenable to high throughput screening and/or multiplexing assays. Other approaches for determining kinase activity utilize fluorescent sensors which undergo a conformational change upon phosphorylation. A majority of fluorescent sensors employed in conventional assays, however, demonstrate very modest fluorescence changes on phosphorylation, which limits their applicability.

Accordingly, it would be advantageous to develop new methods, particles, and kits for determining kinase activity within an assay, particularly ones that are suitable for high throughput screening and/or multiplexing.

SUMMARY OF THE INVENTION

The following description of various embodiments of methods, particles, and kits for determining kinase activity is not to be construed in any way as limiting the subject matter of the appended claims.

An embodiment of a method for processing a particle includes exposing a fluorescent particle to an assay, wherein the fluorescent particle includes a support substrate having one or more fluorescent materials and a peptide substrate coupled to the support substrate via a functional group of the support substrate. The method further includes phosphorylating the peptide substrate during exposure of the fluorescent particle to the assay and processing the fluorescent particle such that the peptide substrate is dephosphorylated and a polarized carbon to carbon double bond (hereinafter referred to as a polarized double bond) is generated at a dephosphorylated site. In addition, the method includes coupling a fluorescent reporter having a nucleophilic terminal group to the fluorescent particle via the polarized double bond.

An embodiment of a particle includes a support substrate having one or more fluorescent materials and a peptide substrate coupled to the support substrate via a functional group of the support substrate.

An embodiment of a kit for detecting an amount of kinase activity within a sample includes a plurality of fluorescent particles and one or more kinase-specific peptide substrates. Each of the plurality of fluorescent particles includes a support substrate with one or more fluorescent materials configured to emit fluorescence in a first wavelength range.

An embodiment of a method for detecting an amount of kinase activity within a sample includes exposing a pooled population of different subsets of fluorescent particles to the sample. At least some of the fluorescent particles include a support substrate with one or more fluorescent materials configured to emit fluorescence in a first wavelength range, wherein at least some of the different subsets of fluorescent particles respectively include a different configuration of the one or more fluorescent materials. In addition, at least some of the fluorescent particles include a peptide substrate coupled to the support substrate via a functional group of the support substrate, wherein at least some of the different subsets of fluorescent particles respectively include a different peptide substrate. The method further includes exposing the sample and the pooled population to a phosphorylation process configured to add phosphate groups to accepting residues of the peptide substrates.

Furthermore, the method includes subsequently processing a plurality of the fluorescent particles such that if any phosphorylated peptide substrates exist among the plurality of fluorescent particles, the phosphorylated peptide substrates are dephosphorylated and polarized double bonds are generated at dephosphorylated sites of the peptide substrates. Moreover, the method includes further processing the plurality of the fluorescent particles such that if any polarized double bonds exist among the dephosphorylated sites of the peptide substrates, fluorescent reporters are coupled to the fluorescent particles at positions of the polarized double bonds via nucleophilic terminal groups of the fluorescent reporters. Such fluorescent reporters are configured to emit fluorescence in a second wavelength range distinct from the first wavelength range. The method also includes subsequently measuring fluorescence emissions of the plurality of the fluorescent particles and identifying subset classifications of the particles in the sample based upon measured fluorescence emissions within the first wavelength range. In addition, the method includes determining, based upon the existence of or lack of measured fluorescence emissions within the second wavelength range, an amount of kinase activity within the sample when the sample and the pooled population are exposed to the phosphorylation process.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In general, the term "particle" as used herein may refer to any substrate used for the analysis of chemistry and biological assays and may specifically refer to articles used to provide and/or support molecular reactions for the qualification and/or quantification of an analyte of interest including but not limited to kinase activity. In addition, the term "particle" may reference articles of a broad range of sizes, such as but not limited to articles having dimensions between approximately 1 nm approximately 300 µm. Hence, the term "particle" may refer to a number of different materials and configurations, including but not limited to microspheres, beads, polystyrene beads, microparticles, gold nanoparticles, quantum dots, nanodots, nanoparticles, composite particles (e.g., metal-polymeric particles or magnetite-polymeric particles), nanoshells, nanorods, nanotubes, microbeads, latex particles, latex beads, fluorescent beads, fluorescent particles, colored particles, colored beads, tissue, cells, micro-organisms, spores, organic matter, any non-organic matter, or any combination thereof. Accordingly, any of such terms may be interchangeable with the term "particle" used herein.

Figure 1:
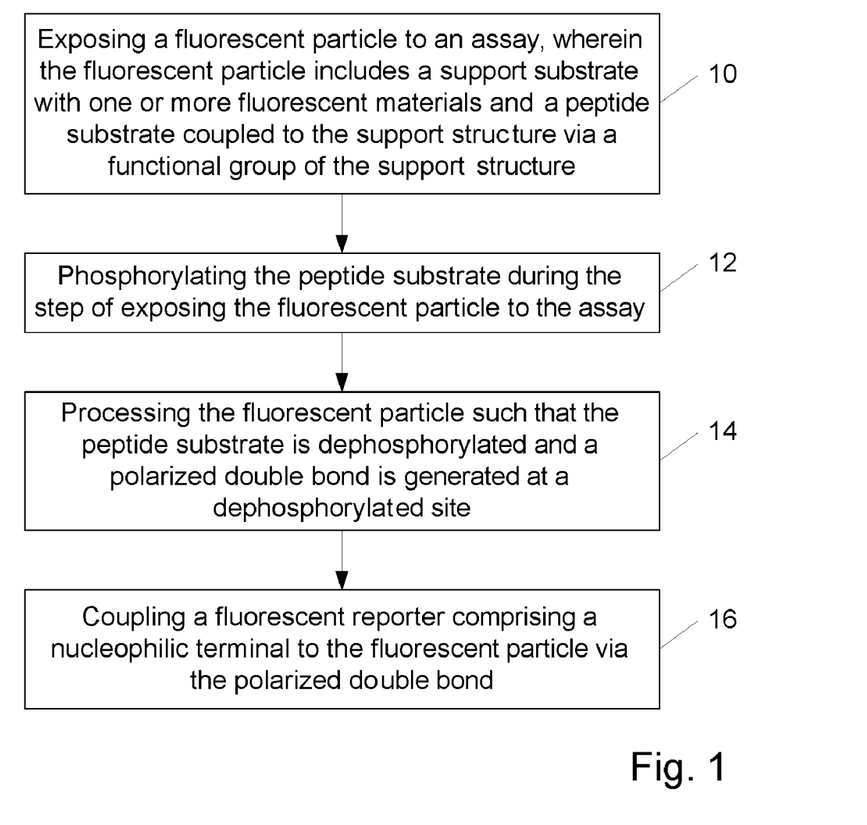
FIG. 1 depicts a flowchart of a method for processing a fluorescent particle for kinase detection.

Turning to the drawings, a flowchart of a method for processing a fluorescent particle for kinase detection is shown in FIG. 1. As shown in FIG. 1, the method may include block 10 in which a fluorescent particle is exposed to an assay. The assay may be a biological assay or a chemical assay. Block 10 specifies the fluorescent particle include a support substrate having one or more fluorescent materials and a peptide substrate coupled to the support substrate via a functional group of the support substrate. As noted above, the term "particle" as used herein may refer to any substrate used for the analysis of chemistry and biological assays and, as such, the term "fluorescent particle" may include any of such substrates comprising one or more photoluminescent materials (e.g., fluorophores, fluorescent dyes, or other fluorescent materials). Although embodiments are described herein with respect to fluorescent dyes, it is to be understood that the embodiments described herein may be used with any photoluminescent material (e.g., a fluorophore or a quantum dot). The photoluminescent materials may be incorporated into the support substrates and/or may be coupled to a surface of the support substrates. In some embodiments, it may be particularly advantageous to crosslink the support substrate in order to incorporate multiple photoluminescent materials within the support substrate. Such embodiments may be particularly applicable for multiplexing assays such that particle classifications on the order of 100 or more may be obtained. The support substrate of the fluorescent particle may include any of those used for the analysis of chemistry and biological assays, including but not limited to polystyrene, metal, or a composite of core and shell materials.

As noted above, in addition to the support substrate of the fluorescent particle having one or more fluorescent materials, the fluorescent particle includes a peptide substrate coupled to the support substrate via a functional group (e.g., COOH, $NH_2$, OH, etc.) of the support substrate. More specifically, the fluorescent particle may include a kinase-specific peptide substrate coupled to the support substrate and, in some cases, coupled to the support substrate via a covalent bond. In this manner, the peptide substrate may be susceptible to phosphorylation as noted in block 12 of the flowchart depicted in FIG. 1. In particular, block 12 in FIG. 1 denotes the method including phosphorylating the peptide substrate during the step of exposing the fluorescent particle to the assay. Such a phosphorylation process may be conducted in the presence of ATP as well as a kinase. The kinase may be readily available in the sample or may be added for the phosphorylation process. The determinants of specificity for kinases are not well understood, although it is understood that both the amino acid sequence motif surrounding the serine/threonine/tyrosine residues of the peptide substrate and the three-dimensional structure of the substrate contribute to the specificity.

In any case, the phosphorylation process may be observed on serine, threonine or tyrosine residues of the peptide substrate. In some embodiments, the phosphorylation process may be conducted in the presence of an ionic liquid. It is theorized that ionic liquids may enhance the rate of phosphorylation, decreasing the processing time of the method, and/or reduce the generation of byproducts which may hinder the subsequent processing of the fluorescent particle, particularly those processes described below in reference to blocks 14 and 16. In some cases, the ionic liquid used to enhance the phosphorylation process may be heated via microwaves. In general, microwave heating may further enhance the rate of phosphorylation. More specifically, utilizing an ionic liquid heated via microwaves may reduce the time needed to complete the phosphorylation process to several minutes rather than several hours.

Subsequent to phosphorylating the peptide substrate, the fluorescent particle may be removed from the sample such that the fluorescent particle may be subsequently processed for the determination of kinase activity as described in more detail below. In some embodiments, the support substrates of the fluorescent particles may be magnetic and the removal process may involve the application of a magnetic field to immobilize the particles while the supernatant is removed. Such an embodiment may advantageously simplify the removal of the particles from the sample and possibly avoid time consuming filtration steps. In yet other cases, however, the support substrates of the fluorescent particles may not be magnetic and the particles may be removed via filtration.

Continuing to block 14 in FIG. 1, the method includes processing the fluorescent particle such that the peptide substrate is dephosphorylated and a polarized double bond is generated at a dephosphorylated site of the peptide substrate. The dephosphorylation process may be conducted by a base catalyzed beta elimination process. In general, the beta elimination process may include any base sufficient to catalyze the process. Examples of bases include but are not limited to sodium hydroxide and tetramethyl ammonium hydroxide (TMA). In some cases, it may be advantageous to employ milder bases (i.e., bases having a pH less than 14), such as TMA, to reduce the amount of byproducts produced from the process. In some embodiments, an ionic liquid may be combined with a milder base to further lessen the generation of byproducts. In yet further embodiments, the base and ionic liquid may be heated via microwaves to increase the rate of the beta elimination reaction. In any case, the beta elimination process is configured to remove the phosphate group from the peptide substrate and replace it with a polarized double bond. The polarized double bond may be referred to as a Michael acceptor, which may used in a subsequent Michael-type addition reaction as described in more detail below in reference to block 16.

As shown in FIG. 1, the method includes block 16 in which a fluorescent reporter having a nucleophilic terminal group is coupled to the fluorescent particle via the polarized double bond. The reaction may generally be referred to as a Michael-type reaction, which may be generally defined as addition of a nucleophilic atom to a compound containing a polarized double bond. The compound containing the nucleophilic atom is commonly called the "Michael donor," and the compound containing the polarized double bound is commonly called the "Michael acceptor." As noted above, the polarized double bond generated from the beta elimination reaction described in reference to block 14 may serve as a Michael acceptor. A fluorescent reporter having a nucleophilic terminal group may serve as a Michael donor and react with the polarized double bond of the fluorescent particle to couple the fluorescent reporter to the fluorescent particle via the nucleophilic terminal group. As with the phosphorylation and beta elimination steps described above in reference to blocks 12, the process of coupling the fluorescent reporter to the fluorescent particle may, in some embodiments, be conducted in the presence of an ionic liquid and, in some cases, an ionic liquid heated by microwaves. The inclusion of the ionic liquid may desirably reduce the generation of byproducts during the coupling process, increasing the yield of the ensuing particle composite. In addition, microwave heating may increase the rate of reaction for the coupling process, reducing production time.

In general, the fluorescent reporter may include a compound of any photoluminescent material (e.g., fluorophores, fluorescent dyes, or other fluorescent materials) with a nucleophilic terminal group coupled thereto. In addition, the nucleophilic terminal group may include any nucleophile, such as but not limited to thiol and amino groups. In some embodiments, it may be desirable to employ hydrophilic fluorescent compounds within the fluorescent reporter to insure a strong fluorescence signal may be subsequently measured. In particular, assays are typically conducted in an aqueous medium. If a hydrophobic dye is used in an aqueous medium, it gets quenched and fluorescence signal is affected. The presence of thiol may, in some embodiments, impart hydrophilicity and, therefore, may be preferred as a nucleophilic terminal group of a fluorescence reporter in some cases. Although there is some ambiguity in the categorizations of hydrophilic compounds and hydrophobic compounds in the chemical arts, the reference of hydrophilic compounds as used herein may specifically refer to compounds which do not dissolve in an organic solvent (e.g., ethyl acetate).

In addition or alternative to being hydrophilic, the fluorescent compound of the fluorescent reporter may be configured to emit fluorescence within a different wavelength range than the one or more fluorescent materials within the support substrate of the fluorescent particle. In this manner, the fluorescence emissions from the different fluorescent materials within the support structure and the fluorescence reporter may not overlap. Such a feature may be particularly advantageous for embodiments in which the fluorescent materials within the support structure are used to categorized particles within a sample. More specifically, a variation of fluorescence ranges among the fluorescent materials may allow different particle categorizations within a sample to be detected without interfering with the detection of kinase activity within the sample. In some cases, the fluorescent compound of the fluorescent reporter may be configured to emit fluorescence within a wavelength range greater than approximately 500 nm since many assays include molecules having intrinsic fluorescence at wavelengths less than approximately 450 nm. In some embodiments, an assay may not be configured with such generalities and, therefore, the configuration of the fluorescent reporter's fluorescence emissions may vary among different applications. For example, in some embodiments, the fluorescent compound of the fluorescent reporter may be configured to emit fluorescence within a wavelength range between approximately 400 nm and approximately 580 nm.

In some cases, the fluorescent reporter may include one or more spacer compounds interposed between the nucleophilic terminal group and the fluorescent compound. The inclusion of one or more spacer compounds may lessen the interference of kinase activity detection and the recognition process between the enzyme and the substrate. In some embodiments, spacer compounds which collectively include between approximately 1 atom and approximately 25 atoms may be used to provide sufficient spacing between the nucleophilic terminal group and the fluorescent compound. In more specific cases, spacer compounds which collectively include between approximately 5 atoms and approximately 25 atoms may be used. It is noted that spacer compounds which collectively include greater than 25 atoms may be used in some applications, depending on the specifications of the fluorescent particle and/or fluorescent reporter. Examples of some spacer compounds having nucleophilic terminal groups that may be employed with fluorescence compounds for the fluorescence reporters are noted below. It is noted that such a listing is exemplary and does not exclude the consideration of other compounds for the fluorescence reporters described herein. Other examples of spacer compounds are noted below in the listing of exemplary fluorescent reporters that may be used for the methods described herein.

Examples of Michael Donors

Examples of Fluorescence Reporters

An exemplary scheme performing the method described in FIG. 1 is outlined below. It is noted that such a scheme is exemplary and does not exclude the consideration of other schemes which may be used for processing a fluorescent particle for kinase detection. Therefore, the methods described herein are not necessarily restricted to the scheme outlined below. As shown below, a kinase-specific peptide substrate may be coupled to a fluorescent particle via a carboxylic acid functional group of the fluorescent particle. As noted above in reference to block 10 in FIG. 1, the methods described herein may be applied to fluorescent particles having other functional groups. The coupling process may be performed in the presence of ethyl-dimethylaminopropyl-carbodiimide (EDC) and sulfonated n-hydroxysuccinimide, but other reagents may be used. Subsequent to coupling the kinase-specific peptide substrate to the fluorescent particle, a phosphorylation process may be performed on the peptide substrate. As noted in the outlined scheme, the phosphorylation process may be performed in the presence of a kinase and ATP and, in some cases, an ionic liquid. After a phosphate group is added to the peptide substrate, the process continues to a beta-elimination step in which the peptide substrate is dephosphorylated and a polarized double bond is generated at a dephosphorylated site of the peptide substrate. As noted above, such a beta-elimination step may be base-catalyzed and, in some embodiments, may additionally be performed in the presence of an ionic liquid. As noted in the scheme outlined below, the polarized double bond may carry an amino acid-serine. The methods described herein, however, may be configured to generate other amino acid residues, such as amino acid threonine and tyrosine.

Subsequent to the beta-elimination process, a fluorescent reporter is adhered to the fluorescent particle via the polarized double bond. The scheme below outlines two exemplary Michael reactions for coupling fluorescence reporters to the fluorescent particle. One of the Michael reactions includes coupling a fluorescent reporter including a fluorescent compound (referenced as a "reporter dye") bound through an amide bond (CONH bond) to one or more spacer compounds (references as "spacer"). The CONH bond is the result of coupling the fluorescent compound with the one or more spacer compounds, specifically coupling a carboxylic acid functional group of the fluorescent compound to an amino acid functional group of the one or more spacer compounds. The inclusion of the CONH bond is exemplary and, therefore, the methods described herein are not necessarily so restricted. The other Michael reaction depicted in the scheme outlined below includes coupling an exemplary biotin-substituted Michael donor and a Streptavidin conjugated fluorescent compound (referenced as a "reporter dye") to the fluorescent particle. An exemplary fluorescent compound which may be particularly suitable for such a reaction is Phycoerythrin (PE). However, other fluorescent compounds as well as other biotin-substituted Michael donors may be used for the methods described herein.

Denotes fluorescent magnetic or non-magnetic beads

Due to the method outlined in FIG. 1, a number of fluorescent particles are described herein. In particular, a number of different fluorescent particle configurations are provided as a result of each of the processing steps of the method. For example, a particle is provided which includes a support substrate with one or more fluorescent materials and a peptide substrate coupled to the support substrate via a functional group of the support substrate. In some embodiments, the peptide substrate may be configured for specific kinase activity, such as for the particle described in reference to block 10 of FIG. 1. In other cases, the peptide substrate may be a phosphorylated peptide substrate, resulting from the phosphorylation step described in reference to block 12 of FIG. 1. In yet other cases, the peptide substrate may include a Michael acceptor as a result of the processing step described in reference to block 14 in FIG. 1. Yet further, the fluorescent particle may include a fluorescent reporter coupled to the peptide substrate as a result of the processing step described in reference to block 16 in FIG. 1. The fluorescent reporter may include any of the embodiments described above in reference to block 16 and, for the sake of brevity, are not reiterated here.

In addition to the method described in reference to FIG. 1 and the resulting particles, various kits for performing the method described in reference to FIG. 1 are provided. In particular, a kit is provided which includes a plurality of fluorescent particles and one or more kinase-specific peptide substrates. Each of the plurality of fluorescent particles includes a support substrate with one or more fluorescent materials configured to emit fluorescence in a first wavelength range. In some cases, the one or more kinase-specific peptide substrates are coupled to the support substrates via functional groups of the support substrates. In specific embodiments, the one or more kinase-specific peptide substrates may be respectively coupled to different subsets of the plurality of fluorescent particles. In this manner, a number of different kinase activities may be evaluated within a sample and, thus, determination of kinase activity may be multiplexed. In other cases, however, the one or more kinase-specific peptide substrates are isolated from the plurality of fluorescent particles. In such embodiments, the kit may, in some cases, further include a reagent configured to couple the one or more kinase-specific peptide substrates to functional groups of the support substrates. In this manner, the kit may be configured to produce particles with the features described in reference to block 10 in FIG. 1.

In some cases, the kit may also include a phosphorylation reagent configured to phosphorylate the one or more kinase-specific peptide substrates to produce particles with the features described in reference to block 12 in FIG. 1. Moreover, the kit may include beta-elimination reagent configured to dephosphorylate the one or more kinase-specific peptide substrates and generate Michael acceptors at the dephosphorylation sites of the one or more kinase-specific peptide substrates to produce particles with the features described in reference to block 14 in FIG. 1. Further yet, the kit may include one or more fluorescent reporter reagents each having a nucleophilic terminal group and one or more fluorescent compounds to produce particles with the features described in reference to block 16 in FIG. 1. The fluorescent compounds of the fluorescent reporter reagents may include any of the embodiments described above in reference to block 16 and, for the sake of brevity, are not reiterated here. In addition to the aforementioned components, the kit described herein may be configured such that at least one of the phosphorylation reagent, the beta-elimination reagent, and the one or more fluorescent reporter reagents includes an ionic liquid. Alternatively stated, the kit may be configured such that any one or multiple of the reagents may be used in the presence or the absence of an ionic liquid. In any case, the kit may contain other ingredients which are considered standard for assay preparation, such as but not limited to a fluorescent label, a competitor molecule, a reference material, wash buffer, plasticware, etc.

Figure 2:
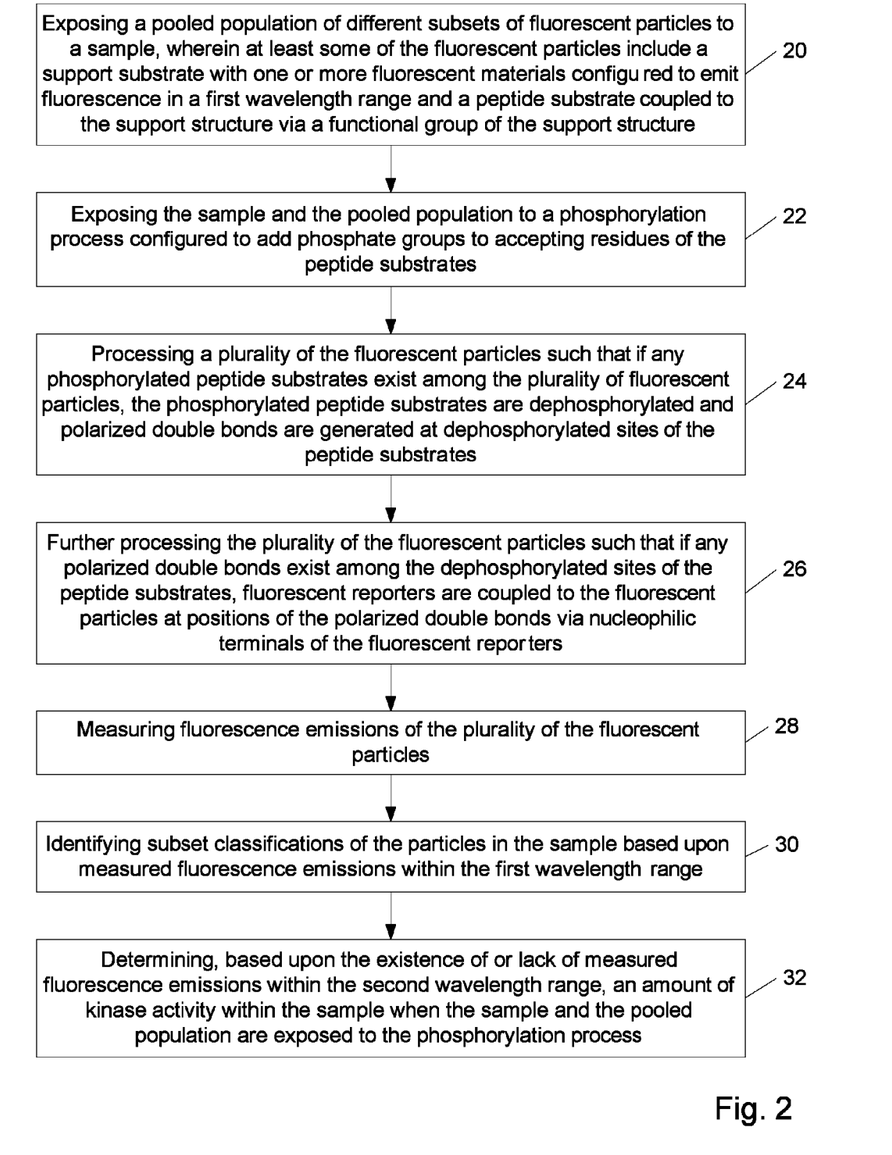
FIG. 2 depicts a flowchart of a method for determining kinase activity within a sample using a multiplexing assay scheme.

As noted above, a method for determining kinase activity within a sample using a multiplexing assay scheme is outlined in a flowchart in FIG. 2. As shown in FIG. 2, the method may include block 20 in which a pooled population of different subsets of fluorescent particles are exposed to a sample. The sample may include any biological or chemical assay in which multiple analytes are desired to be analyzed. At least some of the fluorescent particles within the pooled population include a support substrate with one or more fluorescent materials configured to emit fluorescence in a first wavelength range and a peptide substrate coupled to the support substrate via a functional group of the support substrate. Such particles may be similar to the fluorescent particle described in reference to block 10 of FIG. 1.

To facilitate a multiplexing scheme in which multiple analytes within the sample are detected and/or quantified; the fluorescent particles are configured into distinguishable groups. In some cases, the groups are differentiated by different types and/or concentrations of fluorescent materials absorbed into particles and/or bound to the surface of particles. Consequently, in some embodiments, at least some of the different subsets of fluorescent particles within the pooled population may respectively include a different configuration of the one or more fluorescent materials. In one example, employing two dyes at 10 different concentrations among a set of particles produces 100 fluorescently distinguishable particle categories. The number of particle categories may be augmented by increasing the number of dyes and/or different dye intensities. In many cases, it is advantageous to configure an assay for analysis for several analytes, such as on the order of 100 or more different analytes so that time and processing costs may be minimized in evaluating a sample. It is noted that particle classifications may be facilitated in other manners, such as by particle size and, consequently, the method described in reference to FIG. 2 is not necessarily limited to having subsets of particles with different configurations of fluorescent materials. In addition to having differentiating classification parameters, at least some of the different subsets of fluorescent particles may, in some cases, respectively include a different peptide substrate. In this manner, a number of different kinase activities may be evaluated within the sample and, thus, determination of kinase activity may be multiplexed along with the identification of particles within the sample.

Continuing to block 22, the method includes exposing the sample and the pooled population to a phosphorylation process that is configured to add phosphate groups to accepting residues of the peptide substrates (e.g., serine, threonine or tyrosine residues). Such a process may be similar to the phosphorlating process described in reference to block 12 in FIG. 1 and, therefore, is referenced for the sake of brevity. Block 22 differs slightly from the process described in block 12 in that the sample and pooled population are exposed to a phosphorylation process. The matter of whether the peptide substrate is phosphorylated depends on the nature of the sample to inhibit or promote kinase activity. In particular, it is noted that in some embodiments the peptide may not be phosphorylated by the process described in reference to block 22 due to kinase inhibitors within the sample. In such cases, the method described in FIG. 2 may be used to determine negligible or no kinase activity within the sample. Conversely, in embodiments in which kinase activity is not inhibited (or even promoted) within a sample, the method described in FIG. 2 may be used to determine the degree of kinase activity. As such, although the processing steps of the method outlined in FIG. 2 are configured to process a fluorescent particle in a similar manner as described in FIG. 1, the method in FIG. 2 is slightly different in that the particles may not be altered by the processing steps. Rather the method in FIG. 2 merely exposes the particles to processing steps configured to alter the particles in the event kinase activity is present. In this manner, the method may be used to determine a degree of kinase activity within the sample including embodiments in which no or negligible activity is present. A similar differentiation between blocks 24 and 26 of FIG. 2 (which are described in more detail below) and blocks 14 an 16 may be made as well.

As shown in FIG. 2, the method for determining kinase activity within a sample continues to block 24 in which a plurality of the fluorescent particles are processed such that if any phosphorylated peptide substrates exist among the plurality of fluorescent particles, the phosphorylated peptide substrates are dephosphorylated and polarized double bonds are generated at dephosphorylated sites of the peptide substrates. Such a process may be similar to the process described in reference to block 14 in FIG. 1 and, therefore, is referenced for the sake of brevity. In addition, the method may include block 26 for further processing the plurality of the fluorescent particles such that if any polarized double bonds exist among the dephosphorylated sites of the peptide substrates, fluorescent reporters are coupled to the fluorescent particles at positions of the polarized double bonds via nucleophilic terminal groups of the fluorescent reporters. Such a process may be similar to the process described in reference to block 16 in FIG. 1 and, therefore, is referenced for the sake of brevity. In addition, the description of different embodiments of fluorescent reporters described for block 16 may be referenced for block 26 as well. In some cases, block 26 may include coupling different fluorescent reporters to different subsets of the fluorescent particles. In such cases, the different fluorescent reporters may be configured to emit fluorescence in different wavelength ranges (i.e., distinct from each other as well as the wavelength range of the fluorescence material included in the support structures of the fluorescent particles. In this manner, the different fluorescent reporters may be configured to detect different kinase activity and, therefore, kinase activity detection may be multiplexed in the assay.

A further step of the method includes block 28 in which fluorescence emissions of the plurality of the fluorescent particles are measured. Such a measurement process may be performed by any known measurement process, such as by flow cytometry or fluorescence imaging. The method further includes block 30 in which particle categorizations are determined based upon measured fluorescence emissions within a first wavelength range as specified by the fluorescent materials included with the support structures of the fluorescent particles. More specifically, the output signals generated from fluorescence emitted by the fluorescent materials within the support structures of the particles may be used to categorize the particles into different classification groups. In addition thereto, the method includes determining, based upon the existence of or lack of measured fluorescence emissions within the second wavelength range, an amount of kinase activity within the sample when the sample and the pooled population are exposed to the phosphorylation process as shown by block 32. In particular, since the presence of kinase activity is indicated by the phosphorylation of a peptide substrate and the method described herein recognizes such activity by placing a fluorescent reporter at sites which were previously phosphorylated, fluorescence emissions from the fluorescent reporter may be indicative of a degree of kinase activity within a sample. Conversely, in embodiments in which kinase activity is inhibited within a sample, phosphorylation of a peptide substrate on a fluorescent particle will not occur nor will coupling a fluorescent reporter to a fluorescent particle occur. As a result, no fluorescence emissions will be detected for the wavelength range of the fluorescence reporter, indicating negligible or no kinase activity within the sample.

Further modifications and alternative embodiments of various aspects of the invention may be apparent to those skilled in the art in view of this description. For example, although the methods, particles, and kits are particularly described for determining kinase activity in a sample of a multiplexing scheme, the methods, particles, and kits may alternatively be used for kinase detection in a singleplexing scheme. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A particle, comprising:
   a crosslinked support substrate comprising one or more fluorescent materials;
   a kinase-specific peptide substrate coupled to the crosslinked support substrate via a functional group of the support substrate, wherein upon coupling to the support substrate, the kinase-specific peptide substrate does not include a phosphate; and
   a fluorescent reporter coupled to the kinase-specific peptide substrate via a nucleophilic terminal group of the fluorescent reporter, wherein the fluorescent reporter is configured to emit fluorescence within a different wavelength range than the one or more fluorescent materials of the crosslinked support substrate.

2. The particle of claim 1, wherein the kinase-specific peptide substrate is phosphorylated upon exposure to an assay.

3. The particle of claim 1, wherein the kinase-specific peptide substrate comprises a Michael acceptor.

4. The particle of claim 1, wherein the fluorescent reporter comprises one or more spacer compounds interposed between the nucleophilic terminal group and the fluorescent reporter.

5. The particle of claim 4, wherein the one or more spacer compounds collectively comprise between 1 atom and 25 atoms.

6. The particle of claim 4, wherein the one or more spacer compounds collectively comprise between 5 atoms and 25 atoms.

7. The particle of claim 1, wherein the fluorescent reporter is configured to emit fluorescence at a wavelength between 400 nm and 580 nm.

8. The particle of claim 1, wherein the fluorescent reporter is configured to emit fluorescence at a wavelength greater than 500 nm.

9. The particle of claim 1, wherein the fluorescent reporter comprises a hydrophilic fluorescent material.

10. A particle made by the method comprising:
    incorporating one or more fluorescent materials within or on a crosslinked support substrate to form a fluorescent particle;
    coupling a kinase-specific peptide substrate to the fluorescent particle via a functional group of the crosslinked support substrate;
    exposing the fluorescent particle to an assay subsequent to coupling the kinase-specific peptide substrate to the fluorescent particle;
    phosphorylating the kinase-specific peptide substrate during the step of exposing the fluorescent particle to the assay;
    processing the fluorescent particle such that the kinase-specific peptide substrate is dephosphorylated and a polarized double bond is generated at a dephosphorylated site; and
    coupling a fluorescent reporter comprising a nucleophilic terminal group to the fluorescent particle via the polarized double bond, wherein the step of coupling the fluorescent reporter to the fluorescent particle comprises coupling a fluorescent reporter that is configured to emit fluorescence within a different wavelength range than the one or more fluorescent materials of the crosslinked support substrate.

11. The particle of claim 10, wherein the fluorescent reporter comprises one or more spacer compounds interposed between the nucleophilic terminal group and the fluorescent reporter.

12. The particle of claim 11, wherein the one or more spacer compounds collectively comprise between 1 atom and 25 atoms.

13. The particle of claim 10, wherein the fluorescent reporter is configured to emit fluorescence at a wavelength greater than 500 nm.

14. The particle of claim 10, wherein the step of phosphorylating the kinase-specific peptide substrate comprises exposing the fluorescent particle to an ionic liquid heated via microwaves.

15. The particle of claim 10, wherein the step of processing the fluorescent particle comprises exposing the fluorescent particle to an ionic liquid.

16. The particle of claim 15, wherein the step of processing the fluorescent particle further comprises microwave heating the fluorescent particle and the ionic liquid.

17. The particle of claim 10, wherein the step of coupling the fluorescent reporter comprises exposing the fluorescent particle to an ionic liquid.

18. The particle of claim 17, wherein the step of coupling the fluorescent reporter further comprises microwave heating the fluorescent particle and the ionic liquid.

\* \* \* \* \*